(12) United States Patent
Hardin et al.

(10) Patent No.: US 7,996,065 B2
(45) Date of Patent: *Aug. 9, 2011

(54) BIOPSY SITE MARKER DEPLOYMENT DEVICE

(75) Inventors: Terry D. Hardin, Indianapolis, IN (US); Zachary R. Nicoson, Indianapolis, IN (US); Brian Zimmer, Indianapolis, IN (US); Michael E. Miller, Trafalgar, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/839,127

(22) Filed: Jul. 19, 2010

(65) Prior Publication Data

US 2010/0286627 A1    Nov. 11, 2010

Related U.S. Application Data

(63) Continuation of application No. 11/305,141, filed on Dec. 16, 2005, now Pat. No. 7,761,137.

(51) Int. Cl.
*A61B 6/00* (2006.01)

(52) U.S. Cl. ......... 600/431; 600/426; 600/414; 600/420
(58) Field of Classification Search .......... 600/414, 600/426, 431; 604/14–21, 6.16
See application file for complete search history.

(56) References Cited

U.S. PATENT DOCUMENTS 7,761,137 B2 * 7/2010 Hardin et al. ............. 600/431

\* cited by examiner

*Primary Examiner* — Tse Chen
*Assistant Examiner* — Joel F Brutus
(74) *Attorney, Agent, or Firm* — Robert P. Smith

(57) ABSTRACT

A biopsy marker deployment device adapted to selectively deposit a marker in a target location, such as a biopsy site. In one embodiment, the device includes a deployment assembly comprising a cannula adapted to house at least one marker, an outlet aperture defined by a portion of the cannula, and an actuatable pushrod slidably disposed and movable within the cannula. The deployment assembly further comprises a selectively opening outlet door movable between an open position and a closed position. The outlet door is biased in the closed position and at least partially obstructs the aperture in the closed position to prevent a marker from reentering the cannula upon deployment.

12 Claims, 10 Drawing Sheets

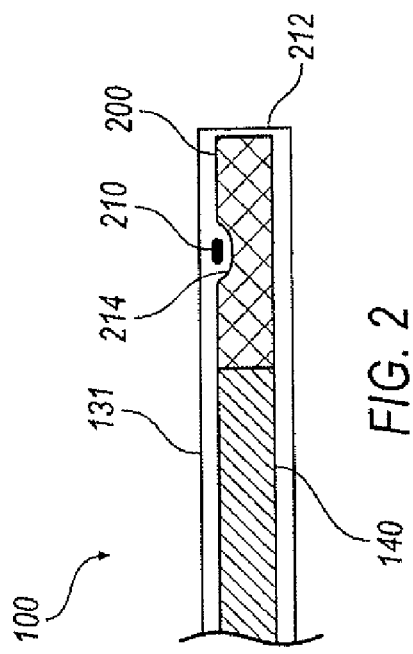
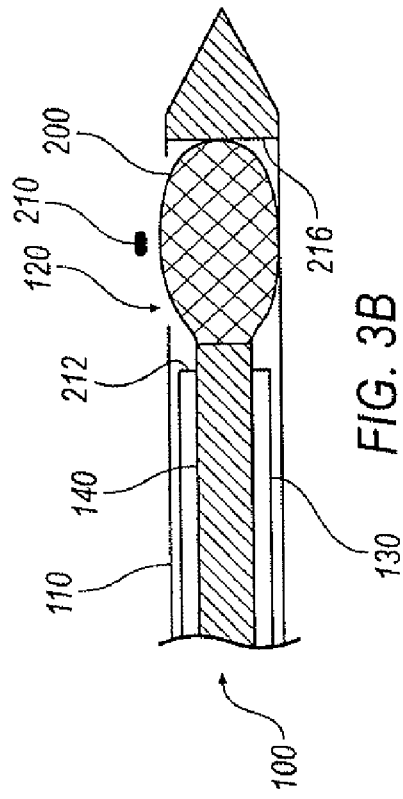
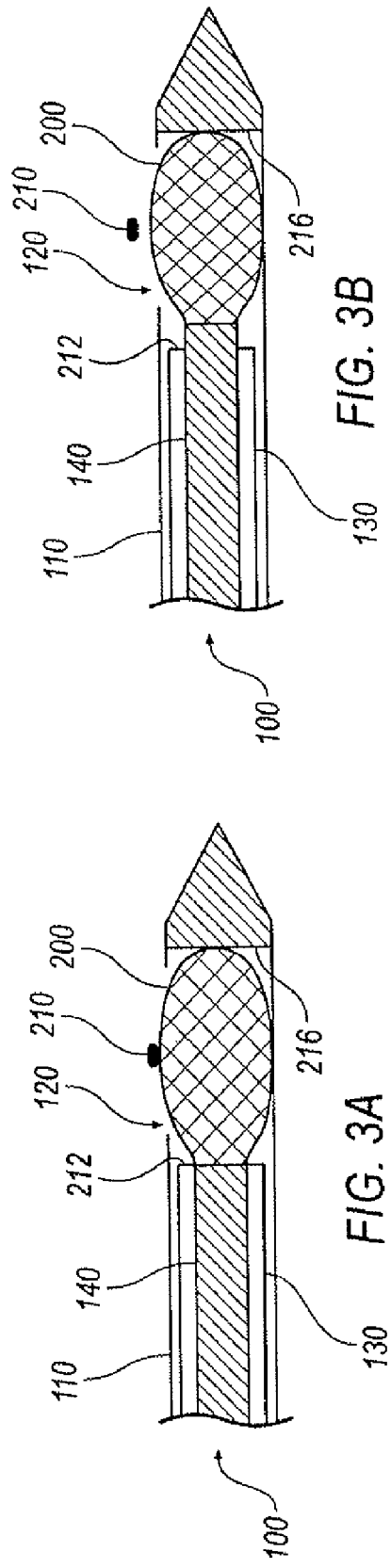

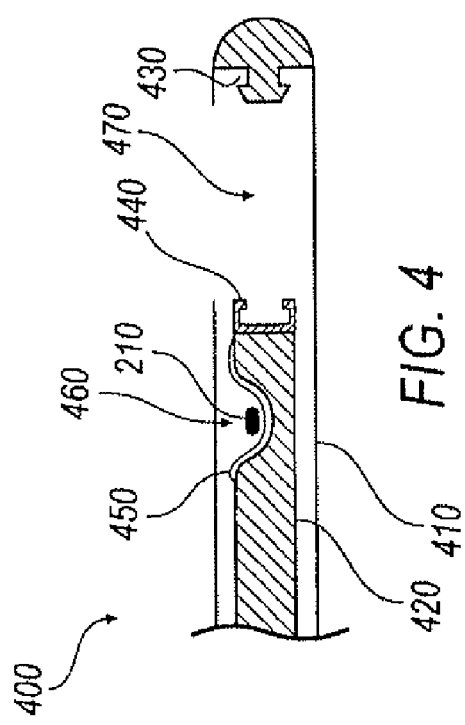
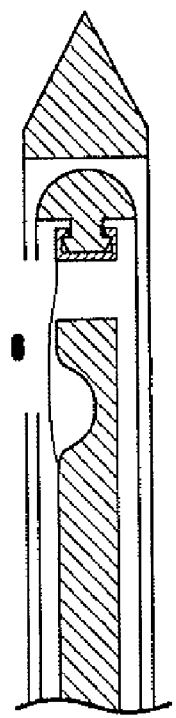
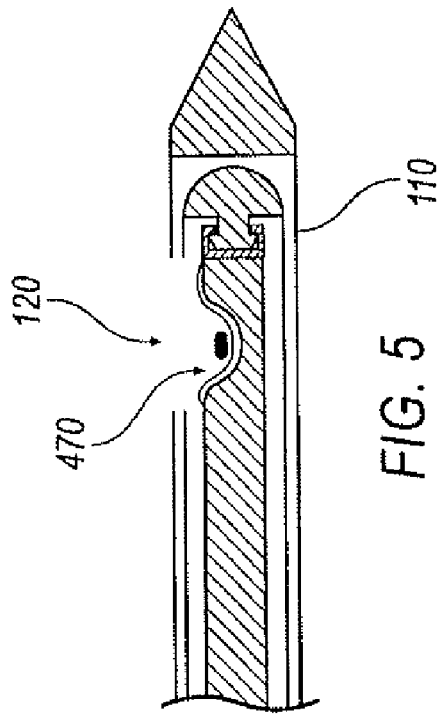
FIG. 4
FIG. 5
FIG. 6

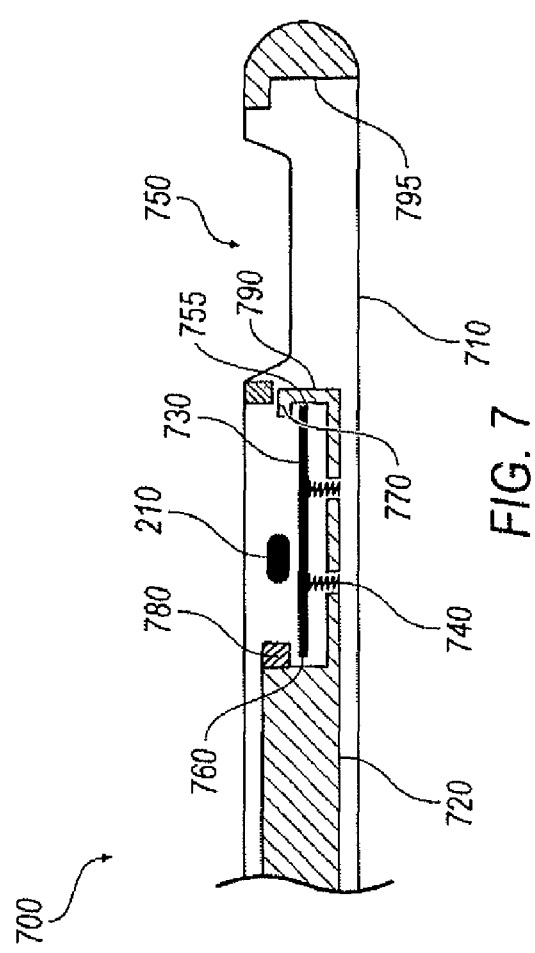
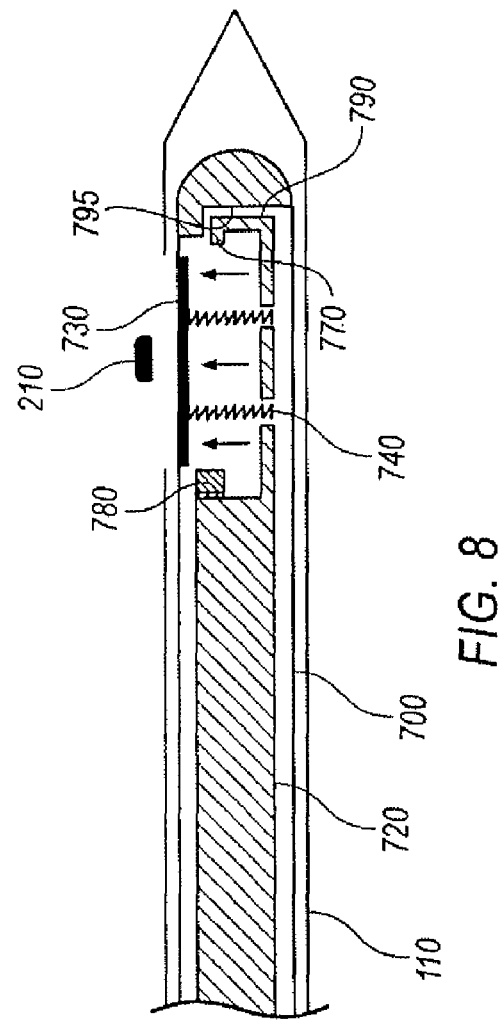
FIG. 7
FIG. 8

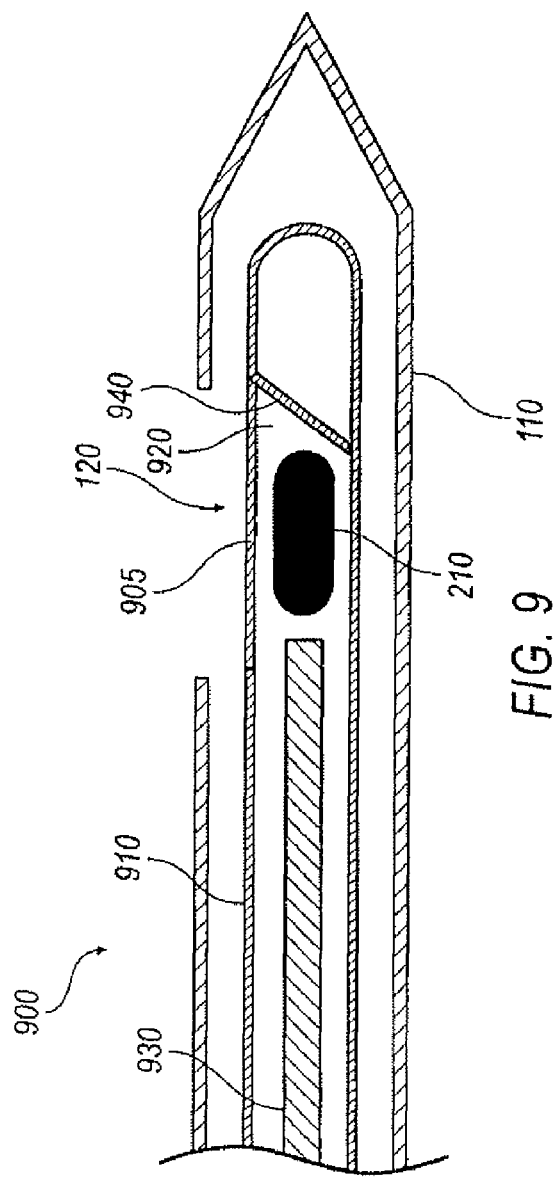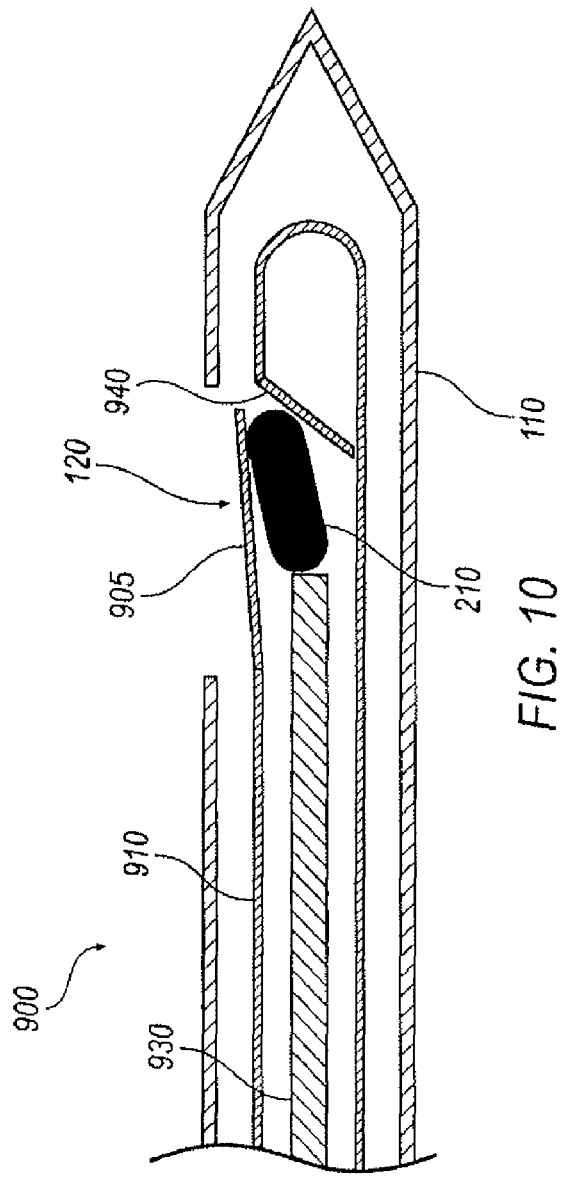

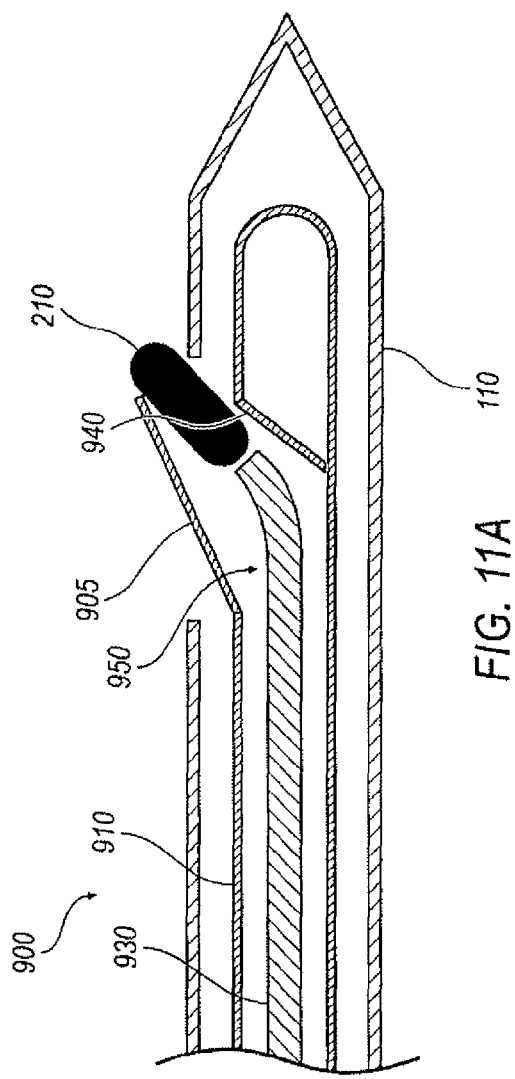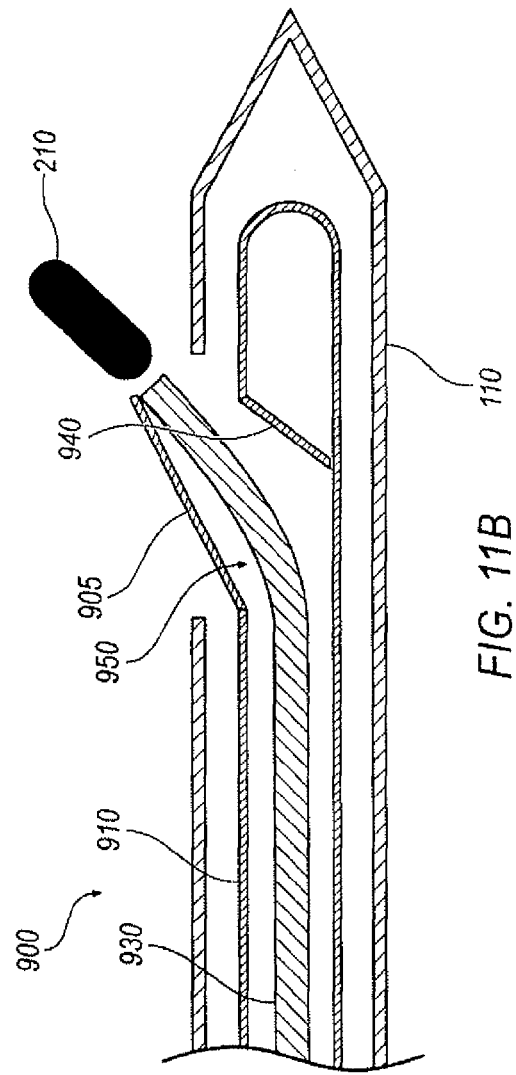
FIG. 11A
FIG. 11B

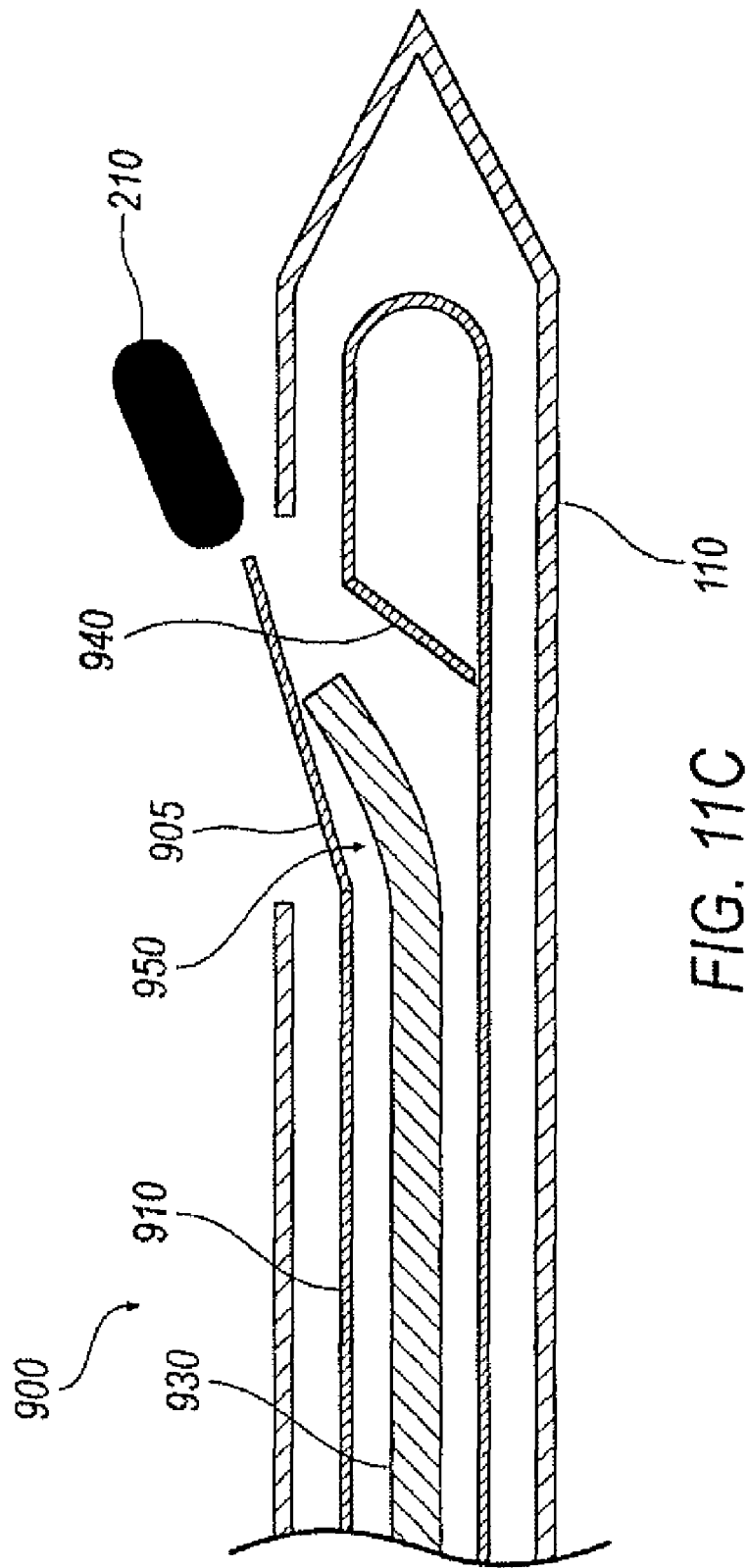

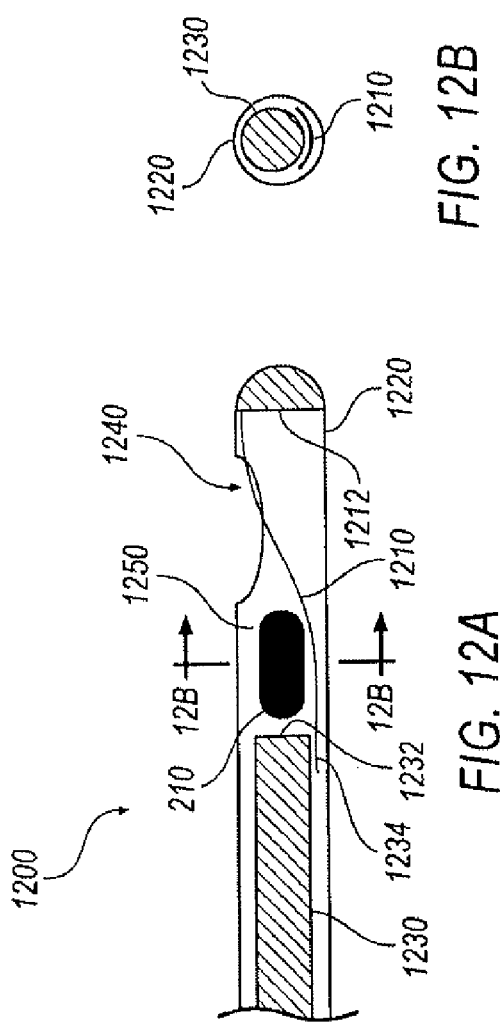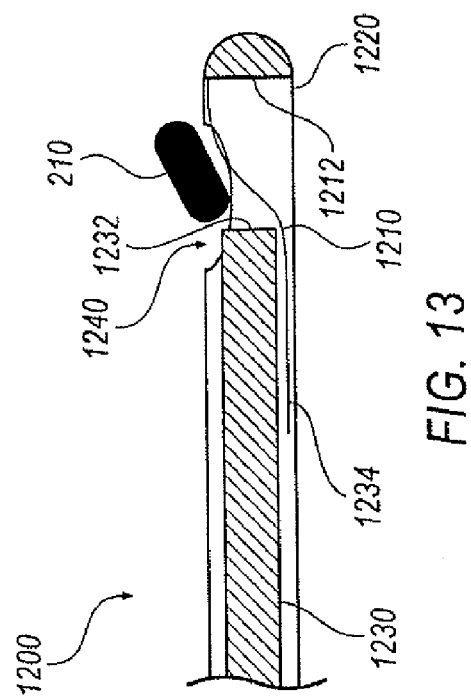

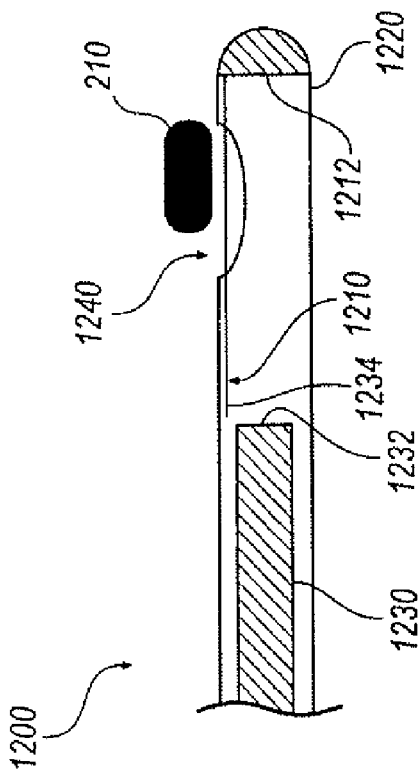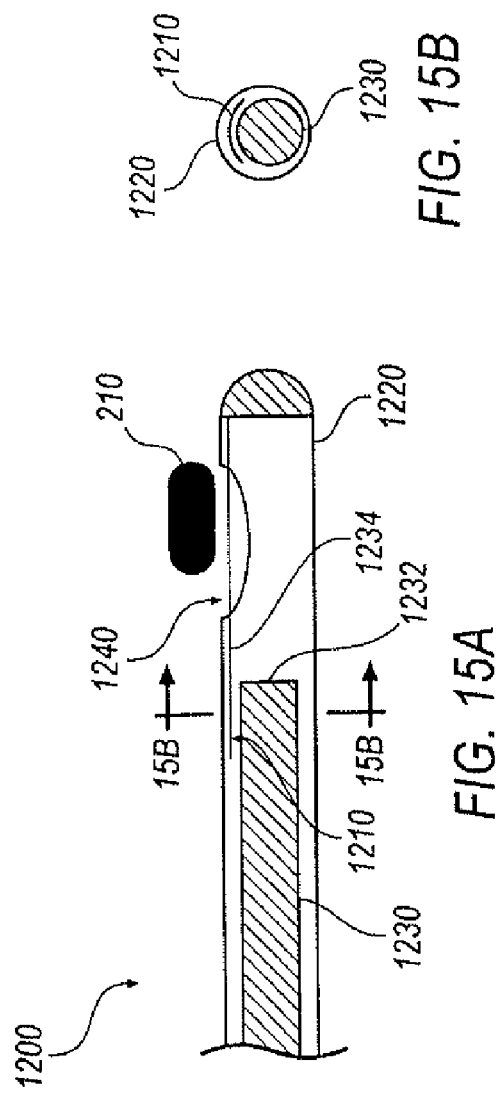

BIOPSY SITE MARKER DEPLOYMENT DEVICE

CROSS-REFERENCE TO RELATED APPLICATIONS

This application is a continuation of U.S. patent application Ser. No. 11/305,141, filed Dec. 16, 2005 now U.S. Pat. No. 7,761,137, which is hereby incorporated by reference in its entirety as part of the present disclosure.

BACKGROUND

Biopsies and other techniques are commonly performed to remove a tissue sample from a selected site within the body. The sample may then be examined and analyzed. Many biopsy devices make use of a hollow tube that forms a working channel. The hollow tube is inserted into the site from where the sample is to be taken. The hollow tube frequently includes an aperture in communication with the working channel. The aperture provides access between the working channel and the site to be analyzed, which may be at some sub-cutaneous depth. This access allows samples to be taken from the desired location.

In particular, the aperture is placed adjacent to the site from which the sample is to be taken. Thereafter, the tissue is drawn through the aperture and into the working channel, such as through the use of a vacuum. A thin tube commonly referred to as a cutting cannula is then pushed through the working channel. The cutting cannula is sized to fit closely to the inner wall of the working channel. Thus, as the cutting cannula is passed over the aperture, the cutting cannula cuts the tissue extending into the working channel. The tissue may then be removed and examined.

It may be desirable to identify or "mark" the location of the biopsy site at some later point. For example, it may be desirable to have the ability to return to the same site, such as to take further samples and/or to provide further treatment to an affected area. In order to identify the biopsy site, markers may be used. The markers frequently include a relatively small device or material that is readily identifiable. The markers are often introduced using a deployment device in conjunction with the working channel of the biopsy device.

When introduced through the working channel of a biopsy device, current marker deployment devices do not effectively close off the aperture, resulting in gaps or dead space between the biopsy device and the marker device. This creates the potential for the marker to fall partially or completely back into the aperture of the biopsy device. As a result, the marker can be pulled out of the biopsy site when the biopsy device is removed. This is known as "drag out." Drag out can lead to the biopsy site not being identified, an incorrect area of tissue being identified, and treatment of the wrong site.

SUMMARY

Marker deployment devices are provided herein for depositing site markers. The markers may be introduced to the biopsy sites through apertures, such as an aperture formed in a working channel of a biopsy device and/or an aperture formed in the deployment device. The deployment devices discussed herein are configured to close the aperture after the marker has been deposited, such that the marker will not fall partially or completely back into the deployment device. This configuration reduces the possibility that the marker will be dragged out when the deployment device is removed.

In one aspect, the invention is directed to a marker deployment device adapted to selectively deploy at least one marker stored therein to a location external the device. The device comprises a cannula defining an axially extending inner lumen adapted to receive at least one marker and an aperture in communication with the inner lumen; and a manually actuatable push rod slidably received and movable within the inner lumen of the cannula, wherein the pushrod, upon actuation, is adapted to contact and urge at least one marker distally through the inner lumen of the cannula. The device further comprises a selectively opening outlet door movable between an open position and a closed position, wherein the door (i) is configured to move to the open position upon contact with at least one of the push rod and at least one marker, (ii) obstructs at least a portion of the aperture when in the closed position and (iii) is biased toward the closed position such that the door moves to the closed position after a marker is deployed through the aperture to prevent the marker from re-entering the cannula upon deployment; and an inclined surface positioned within the inner lumen of the cannula adjacent to the aperture, wherein the inclined surface is adapted to guide at least one marker from the inner lumen toward and through the aperture as the marker is urged by the push rod.

Details of one or more implementations of the invention are set forth in the accompanying drawings and in the description below. Further features, aspects, and advantages of the invention will become apparent from the description, the drawings, and the claims.

BRIEF DESCRIPTION OF THE DRAWINGS

The accompanying drawings illustrate various embodiments of the present system and method and are a part of the specification. The illustrated embodiments are merely examples of the present system and method and do not limit the scope of the disclosure.

FIG. 2 illustrates a cross-sectional view of a distal end of the deployment device of FIG. 1 in more detail.

FIGS. 3A-3B are cross-sectional views that illustrate the deployment action of the deployment device of FIG. 2.

FIG. 4 is illustrates a cross-sectional view of a distal end of an alternative embodiment of a deployment device according to one exemplary embodiment.

FIG. 5 illustrates a cross-sectional view of the deployment device of FIG. 4 at a first position relative to a working channel of a biopsy device.

FIG. 6 is a cross-sectional view of the deployment device of FIG. 4 illustrating the deployment action of the deployment device.

FIG. 7 illustrates a cross-sectional view of another embodiment of a deployment device in a first position according to one exemplary embodiment.

FIG. 8 is a cross-sectional view of the deployment device of FIG. 7 illustrating the deployment action of the deployment device depositing a marker.

FIG. 9 illustrates a cross-sectional view of another embodiment of a deployment device according to one exemplary embodiment.

FIG. 10 illustrates a cross-sectional view of the deployment device of FIG. 9 in the process of deploying a marker.

FIG. 11A illustrates a cross-sectional view of the deployment device of FIG. 9 in the process of deploying the marker.

FIG. 11B illustrates a cross-sectional view of the deployment device of FIG. 9 in an intermediate stage of deploying the marker.

FIG. 11C illustrates a cross-sectional view of the deployment device of FIG. 9 in a final stage of deploying the marker.

FIG. 12A illustrates a cross-sectional view of another embodiment of a deployment device according to one exemplary embodiment.

FIG. 12B illustrates a cross-sectional view of a portion of the deployment device of FIG. 12A taken along lines 12B-12B.

FIG. 13 illustrates a cross-sectional view of the deployment device of FIG. 12A in the process of deploying a marker.

FIG. 14 illustrates a cross-sectional view of the deployment device of FIG. 12A after the marker has been deployed by the deployment device and push rod has been retracted.

FIG. 15A illustrates a cross-sectional view of the deployment device of FIG. 12A after the marker has been deployed and the push rod has secured a flexible member in place.

FIG. 15B illustrates a cross sectional view of the deployment device of FIG. 15A taken along lines 15B-15B.

Throughout the drawings, identical reference numbers designate similar, but not necessarily identical, elements.

DETAILED DESCRIPTION

An apparatus is provided herein for deployment of a marker. The marker is delivered by way of a lumen, such as the working channel of a biopsy device or through the channel formed when performing a biopsy. According to several exemplary embodiments discussed below, the marker deployment device includes an elongated introduction device and a deployment assembly. The deployment assembly deposits the marker through an aperture, and then at least substantially closes the aperture. Maintaining the aperture in a substantially closed position reduces the possibility that the marker will fall back into deployment device.

In the following description, for purposes of explanation, numerous specific details are set forth in order to provide a thorough understanding of the present method and apparatus. It will be apparent, however, to one skilled in the art that the present method and apparatus may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
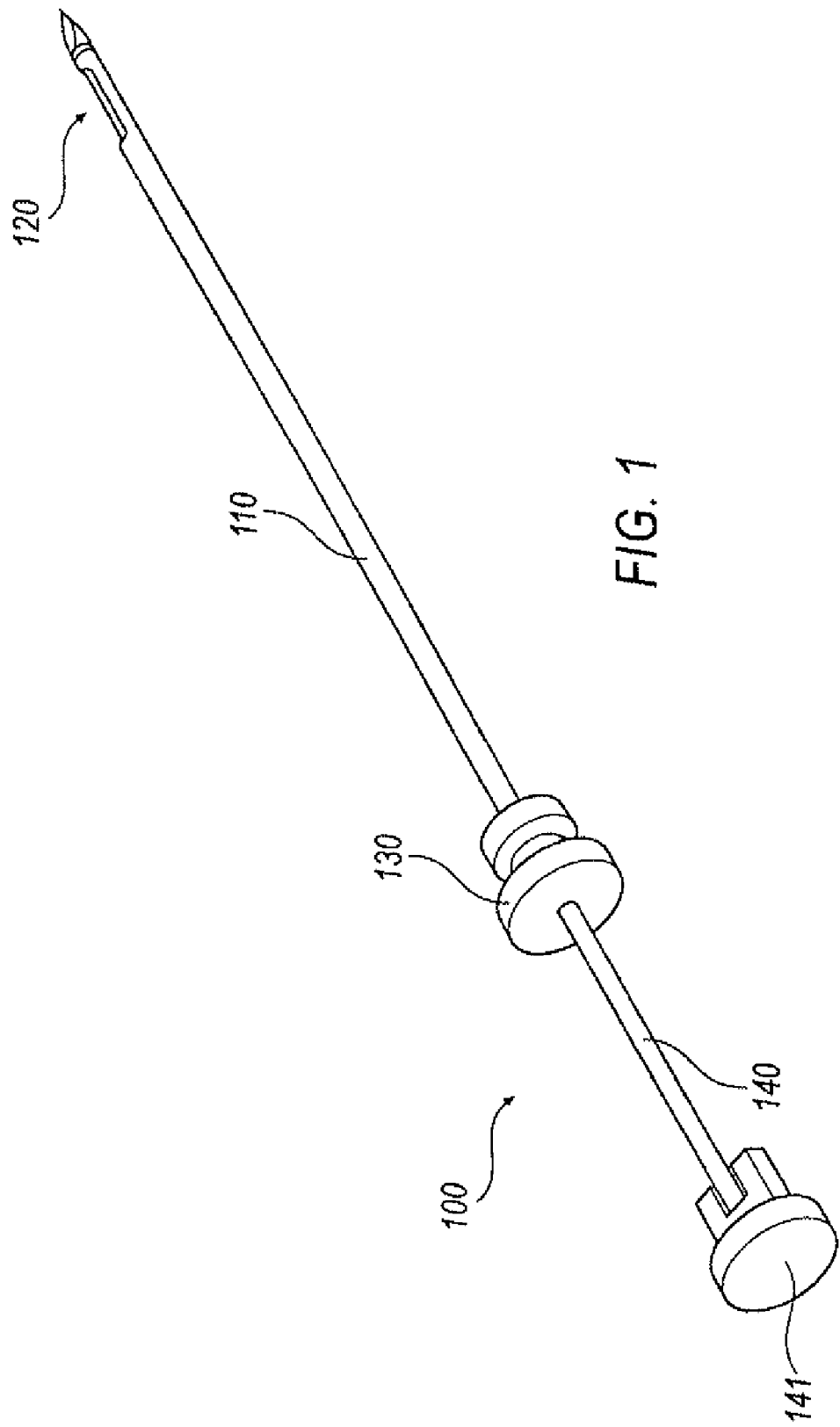
FIG. 1 illustrates a perspective view of a deployment device according to one exemplary embodiment.

FIG. 1 illustrates a marker deployment device (100) coupled to a working channel (110), such as the working channel of a biopsy device according to one exemplary embodiment. The working channel (110) has an aperture (120) defined therein. The deployment device (100) according to the present exemplary embodiment may include a hub (130) to which a cannula (131), (as best seen in FIG. 2) is connected. The cannula is selectively received within the working channel (110).

The deployment device (100) also includes a push rod (140), which extends into the hub (130). In FIG. 1, a relatively large portion of the hub (130) is shown in contact with the proximal end of the working channel (110). This contact prevents further movement of the deployment device (100) within the working channel (110). As the movement and location of the deployment device (100) is thus constrained, the push rod (140) may then be advanced to deploy a marker.

The proximal end of the push rod (140) may include a plunger (141) that is relatively large compared to the rest of the push rod (140), plunger (141) which may facilitate movement of the push rod (140) relative to the working channel (110) as the deployment device (100) is actuated. Other components of the deployment device (100) will be discussed in isolation with reference to FIG. 2, while the operation of the deployment device (100) will be discussed further with reference to FIGS. 3A-3B.

FIG. 2 illustrates a distal end (212) of the deployment device (100) in more detail. As used herein, the distal end shall refer to a portion nearer the biopsy site while proximal shall refer to the end opposite the distal end. As shown in FIG. 2, the marker deployment device (100) includes the cannula (131), the push rod (140), and an expandable member (200). The expandable member (200) forms a deployment assembly. The deployment assembly is configured to deposit a marker (210) while minimizing space between the deployment device (200) and the device or area used to introduce the deployment device. Further as seen in FIG. 2, the distal end (212) of the cannula (130) is open.

The distal end of the push rod (140) is coupled to the expandable member (200). Consequently, translation of the push rod (140) relative to the cannula (131) results in movement of the expandable member (200) relative to the cannula (131). The expandable member (200) is configured to receive a marker (210). In particular, the expandable member (200) may be compressed by a predetermined amount to form a depression (214) appropriately sized such that the marker (210) may be received therein. FIG. 2 illustrates the push rod (140), expandable member (200), and marker (210) retained within the cannula (131) at a first, pre-deployment position. In this first position, the expandable member (200) may be compressed within the cannula (131).

As introduced, according to one exemplary embodiment, the deployment device (100) is delivered through the working channel (110) of a biopsy device or other surgical device. In particular, the cannula (131) is sized to slide relative to the working channel of the biopsy device. Thus, the distal end (212) of the deployment device (100) may be introduced to the proximal end of the working channel (110). As the deployment device is urged toward the distal end of the working channel (110), the push rod (140), the expandable member (200), and the marker (210) are maintained in their first position relative to the cannula (131).

The distal end of the deployment device (100) is urged toward the distal end of the working channel (110) a predetermined distance. In one embodiment, the hub (130) comes into contact with the proximal end of the working channel (110) to serve as a stop member to define the predetermined distance. As hub (130) comes into contact with the proximal end of the working channel (110), the cannula (131) is prevented from advancing further. With the location of the cannula (130) thus constrained, the push rod (140) may be actuated to deploy the marker (210).

The actuation of the push rod (140) is shown in FIGS. 3A-3B. In particular, FIG. 3A illustrates the cannula (130) located within the working channel (110) of the biopsy device. According to the exemplary embodiment shown in FIG. 3A, as the push rod (140) is urged through the distal end of the cannula (130), the expandable member (200) contacts a wall (216) at the distal end of the working channel (110) adjacent aperture (120). As the push rod (140) is further advanced, the expandable member (200) acts against wall (216) and the internal surface of working channel (110) so to expand to fill the working channel (110). As the push rod (140) is urged further toward the distal end of the working channel (110), the expandable member (200) expands through with the aperture (120; best seen in FIG. 3A) in the working channel (110).

The expandable member (200) is expanded, thereby substantially filling the aperture (120). For example, according to one exemplary embodiment, the expandable member (200) is made of a resilient material that is compressed while in the cannula (131) and the working channel (110). Such materials may include, without limitation, nitinol, an expandable mesh material, and/or shape memory material.

According to other exemplary embodiments, the material may be substantially uncompressed or slightly compressed while in the cannula (131) and/or the working channel (110). When the push rod (140) is advanced sufficiently the expandable member (200) comes into contact with the wall (216) at the distal end of the working channel (110). Advancing the push rod (140) compresses the expandable member (200) about its length within the working channel (110). This compression causes the expandable member (200) to expand in a direction perpendicular to the compression. This expansion causes the expandable member (200) to expand through the aperture (120).

As the expandable member (200) expands in a perpendicular direction, it carries the marker (210) through the aperture (120) and into the surrounding biopsy cavity. According to the exemplary embodiment shown in FIG. 3B, the expandable member (200) may be expanded a predetermined amount to thereby deposit the marker (210) into the biopsy cavity. Thereafter, the expansion of the expandable member (200) may be reduced slightly to provide spacing between the expandable member (200) and the deposited marker (210). The expandable member (200) remains sufficiently expanded to substantially fill the aperture (120), thereby sealing the aperture (120) and preventing the marker (210) from falling back into the deployment device (100). Further, after deployment the working channel (110) may be rotated such that the opening (120) is rotated away from the deployed marker (210), thereby further preventing that the marker (210) does not fall back into the working channel (110).

The deployment device (100) may then be withdrawn, such as by withdrawing the working channel (110) with the expandable member (200) expanded to maintain a seal about the aperture (120). Thus, as the deployment device is removed, the aperture remains substantially sealed, thereby minimizing or reducing the possibility that the marker (210) will fall partially or completely into the working channel (110) and thus be dragged out. While the marker deployment device (100) has been described with reference to a working channel (110), those of skill in the art will appreciate that other configurations are possible. For example, according to one exemplary embodiment, the deployment device (100) may be introduced to the biopsy site by way of the tissue track created by a biopsy device in creating the biopsy site. Other configurations are also possible, as will now be discussed in more detail.

FIGS. 4, 5, and 6 illustrate a deployment device (400) that includes a cannula (410), a push rod (420), a protruding member (430), a receiving member (440), and a strip of flexible material (450). FIG. 4 illustrates the deployment device (400) in isolation. FIG. 5 illustrates the deployment device (400) at a first, pre-deployment position relative to a working channel (110). FIG. 6 illustrates the deployment device (400) deploying a marker (210).

As shown in FIG. 4, a seat (460) is defined in the push rod (420). A strip of flexible material, hereinafter referred to as a flexible strip (450), has a first position that is coupled to the receiving member (440). The receiving member is detachably coupled to a distal end of push rod (420). The flexible strip (450) extends from the receiving member (440), and along the surface of a seat (460). A second portion of flexible strip (450) is connected to a portion of push rod (420), adjacent seat (460), opposite receiving member (440). Thus, while in the first position, the marker (210), which is positioned in the seat (460), rests on the flexible strip (450) while the marker (210) is received within the seat (460).

Further, as shown in FIG. 4, the distal end of the cannula (410) is substantially closed. Additionally, a cannula aperture (470) is defined near the distal end of the cannula (410). According to the present exemplary embodiment, the protruding member (430) is disposed at or near the closed distal end of the cannula (410). The protruding member (430) is configured to be matingly coupled to the receiving member (440).

In particular, as shown in FIG. 5, the cannula (410) may be advanced relative to the working channel (110) until the distal end of the cannula (410) comes into contact with the distal end of the working channel (110). At this position, the cannula aperture (470) is aligned relative to the aperture (120) defined in the working channel (110). Thereafter, the push rod (420) may be advanced until the receiving member (440) comes into contact and engages with the protruding member (430). This contact couples the receiving member (440) to the protruding member (430). As the receiving member (440) is coupled to the protruding member (430), the seat (460) is aligned relative to the both the cannula aperture (470) and the aperture (120) defined in the working channel (110).

Thereafter, the push rod (420) may deploy the marker (210) while minimizing the possibility that the marker (210) will fall completely or partially back into the seat (460), the cannula aperture (470), and/or the aperture (120) defined in the working channel (110). Such a configuration is shown in FIG. 6. In particular, as previously discussed, the protruding member (430) is coupled to the receiving member (440). As the push rod (420) is retracted, the protruding member (430) retains the receiving member (440) in contact therewith.

As the push rod (420) is retracted, the first portion of flexible strip (450) is retained in contact with the receiving member (440) and the second portion of flexible strip (450) is retained to a portion of the push rod (420). Consequently, as the distal end of the push rod (420) is retracted while the flexible strip (450) remains stationary, a center portion of flexible strip (450) that is positioned over seat (460) extends upwardly, carrying marker (210) through aperture (470).

As the center portion of flexible strip (450) is driven upward and out of the seat (460), the marker (210) is also upwardly displaced. As introduced, when the distal end of the cannula (410) is in contact with the distal end of the working channel (110), the cannula aperture (470) and the aperture (120) in the working channel (110) are aligned. As the marker (210) is driven upward, it is urged through the cannula aperture (470), through the aperture (120) in the working channel (110), and then deposited into the biopsy site.

As the marker (210) is deposited into the biopsy site, the flexible strip (450) closes the cannula aperture (470) and minimizes the space between the aperture (120) in the working channel (110) and the cannula (410). Thus, as the deployment device (400) and the working channel (110) are removed, the flexible strip (450) minimizes the possibility that the marker (210) will fall partially or completely back into the working channel (110) or cannula (410). While a working channel of a biopsy device has been described in introducing the deployment device to a biopsy site, those of skill in the art will appreciate that the deployment device (400) may be introduced in other ways, such as by the tract formed by the biopsy device when performing the biopsy.

FIGS. 7 and 8 illustrate a deployment device (700) that includes a cannula (710), a push rod (720), a platform (730), and at least one biasing member, such as springs (740). In particular, FIG. 7 illustrates the deployment device (700) in isolation while in a first, pre-deployment position. As seen in FIG. 7, the cannula (710) has a cannula aperture (750) defined therein. While in the first position, the push rod (720) is positioned behind the cannula aperture (750). In this position, the marker (210) is carried by the platform (730). In this position, the springs (740) associated with the platform (730) are retained in a compressed position within the cannula (710) with ends (755, 760) of platform (730) being functionally retained by shoulders (770, 780).

The push rod (720) is advanced to actuate the deployment device, as shown in FIG. 8. As shown in FIG. 8, the deployment device (700) may be introduced to a biopsy site with a working channel (110). More specifically, according to one exemplary embodiment, the cannula (710) is advanced relative to the working channel (110) until the distal end of the cannula (710) comes into contact with the distal end of the working channel (110). As the cannula (710) is thus advanced, the push rod (720) is maintained in the first position described above. Further, as the cannula (710) comes into contact with the distal end of the working channel (110), the cannula aperture (750) is aligned relative to the aperture (120) defined in the working channel (110).

Thereafter, the push rod (720) may be advanced relative to the cannula (710). For example, the push rod (720) may be advanced until a distal end (790) of the push rod (720) contacts an inner wall (795) of cannula (710). In one embodiment, the contact between the inner wall (795) and the distal end (790) of push rod (720) causes the shoulders (770, 780) to flex, thereby releasing the platform (730).

In another embodiment, one of the shoulders (780) is constructed of a compressible material. As the push rod (720) is advanced relative to the cannula (710), the compressible shoulder (780) contacts an abutment that extends downwardly into the cannula (710) adjacent the cannula aperture (750) such that the compressible shoulder (780) compresses, thereby releasing the platform (730).

Once the platform (730) is released, the biasing elements (740) push the platform (730) and the marker (210) carried therein upwardly, thereby deploying the marker (210) into the biopsy cavity. More specifically, as previously introduced, while in the body of the cannula (710), the platform (730) is retained in a compressed position. As the platform (730) is moved into communication with the cannula aperture (750), the biasing elements (740) release the platform (730) from the cannula (710).

According to one exemplary embodiment, the platform (730) and the cannula aperture (750) are slightly larger than the aperture (120) defined in the working channel (110). Thus, as the platform (730) is released, it is urged outward until it comes into contact with the working channel (110). Thus, the platform (730) obstructs the aperture (120). As the platform (730) is thus urged outwardly, the marker (210) is pushed through the aperture (120) and is thus deposited in the biopsy site.

The deployment device (700) may then be removed. The deployment device (700) and working channel (110) may be removed while the platform (730) remains in position to obstruct the aperture (120). Thus, the deployment device (700) is configured to deposit the marker (210) while minimizing the possibility that the marker (210) will fall partially or completely into the working channel (110) and/or the deployment device (700). Accordingly, the deployment device (700) minimizes the possibility of drag out. While a working channel has been described for introducing the deployment device to the biopsy site, those of skill in the art will appreciate that the deployment device (700) may be introduced by any suitable means, such as through the tract cut by a biopsy device in creating the biopsy site.

FIGS. 9, 10, and 11 illustrate a deployment device (900) that includes a selectively opening outlet (905) according to one exemplary embodiment. An exemplary embodiment will be discussed that includes a cannula (910) with the selectively opening outlet (905) coupled thereto. A push rod (930) is received within the cannula (910). As will be discussed in more detail below, the selectively opening outlet (905) allows the marker (210) to be selectively deployed in a biopsy site while minimizing the possibility that the marker will be dragged out as the deployment device (900) is removed.

FIG. 9 illustrates the deployment device (900) in a first, pre-deployment position within a working channel (110). As shown in FIG. 9, the push rod (930) is sized to translate within the cannula (910). A ramp (940) or other inclined surface is formed in the distal end of the inner cannula (910). In the preliminary position, the marker (210) is located in a marker staging cavity (920) defined in the space between the distal end of the cannula (910) and the distal end of the push rod (930). In the first position, the selectively opening outlet (905), and the aperture (120) defined in the working channel (110) are aligned.

The push rod (930) is actuated to selectively open the selectively opening outlet (905) and deposit the marker (210) in a biopsy site. In particular, FIG. 10 illustrates the push rod (930) being advanced toward the ramp (940). The push rod (930) may be flexible or rigid. Alternatively, the push rod (930) may be formed with a flexible material, but also includes a stiffening sleeve therein. Further, the push rod may be formed of any suitable material. Suitable materials include, without limitation, plastic and metallic materials. As the push rod (930) is thus advanced, the distal end of the push rod (930) contacts the marker (210) thereby urging the marker (210) toward the ramp (940). As the marker (210) engages the ramp (940), an end of the marker (210) is urged into contact with the selectively opening outlet (905).

According to one exemplary embodiment, the selectively opening outlet (905) is biased to remain in a closed position. For example, the cannula (910) and selectively opening outlet (905) may be formed of a resilient material, such as a plastic material. Accordingly, the selectively opening outlet (905) may be biased to remain in a closed position. After the marker (210) is moved into contact with the selectively opening outlet (905), continued advancement of the push rod (930) drives the marker (210) further up the ramp (940). In one embodiment, the push rod (930), which may have at least a distal end portion that has a predetermined degree of flexibility is advanced such that the distal end of the push rod is advanced through the selectively opening outlet (905) to insure that the marker (210) fully exits the deployment device (900).

As illustrated in FIG. 11A, the pushrod (930) is advanced and bends at the interface of ramp (940) in a flexion region (950). The marker (210) moves further up the ramp (940) and the marker (210) deflects the selectively opening outlet (905) outwardly. Thus, the bias which maintains the selectively opening outlet (905) closed is overcome and the selectively opening outlet (905) is opened. As illustrated in FIG. 11B, the push rod (930) is further advanced until the marker (210) continues through the selectively opening outlet (905)

through the aperture (120) defined in the working channel (110), and into the biopsy site.

FIG. 11C illustrates the deployment device in a final stage of deploying the marker. As introduced, the selectively opening outlet (905) is biased to stay in a closed position. Thus, as the marker (210) clears the selectively opening outlet (905), the selectively opening outlet (905) returns to a closed position relative to the cannula (910). Accordingly, after the marker (210) has been deposited, the selectively opening outlet (905) closes, thereby closing off the cannula (910) while minimizing any space between the cannula (910) and the working channel (110). Once the marker (210) has been deposited, the deployment device (900) and working channel (110) may be removed without the marker (210) being dragged out. Further, selectively opening outlet (905) closes behind marker (210) and prevents marker (210) from following push rod (930) back within working channel (110). As can be seen with FIGS. 9-11C, the cross section of push rod (930) is smaller than marker (210). The difference in size provides for the selectively opening outlet (905) to "wipe off" marker (210) from the distal end of push rod (930). This "wiping off" action occurs because the bias of selectively opening outlet (905) follows the smaller cross section of push rod (930) and allows the selectively opening outlet (905) to begin closing behind marker (210).

While a working channel has been described for introducing the deployment device to the biopsy site, those of skill in the art will appreciate that the deployment device (900) may be introduced by any suitable means, such as through the tract cut by a biopsy device when creating the biopsy site.

FIGS. 12-15 illustrate a deployment device (1200) that includes a flexible strip (1210) having a first end secured to an internal wall (1212) of a distal end of a cannula (1220). FIG. 12A illustrates the components of the deployment device (1200) in a first, pre-deployment position. As shown in FIG. 12A, the deployment device (1200) also includes a push rod (1230). In the first position, the push rod (1230) has a distal end (1232) that extends over a portion of a proximal end (1234) of the flexible strip (1210) thereby depressing a portion of the flexible strip (1210).

The cannula (1220), according to the present exemplary embodiment, has a cannula aperture (1240) defined therein. The cannula aperture (1240) is adjacent the distal end of the cannula (1220). The distal end of flexible strip (1210) is secured to the internal wall (1212) at the distal end of the cannula (1220) and aligned with the proximal and distal edge of aperture (1240). In the first position, the flexible strip (1210) extends away from the distal end of the cannula (1220) past the cannula aperture (1240) and beyond the distal end (1232) of the push rod (1230).

The flexible strip (1210) is preliminarily and selectively retained in this position by the push rod (1230). More specifically, FIG. 12B illustrates a cross sectional view taken along section 12B-12B As shown in FIG. 12B, in the first position, the proximal end of the flexible strip (1210) is retained between the distal end (1232) of the push rod (1230) and an interior wall of the cannula (1220). With the flexible strip (1210) thus retained, the flexible strip (1210) defines a retaining cavity (1250) that extends into a flexible ramp. In this position, the marker (210) rests on the flexible strip (1210) within the retaining cavity (1250) near the distal end (1232) of the push rod (1230).

The deployment device (1200), according to the present exemplary embodiment, is actuated by advancing the push rod (1230). As the push rod (1230) is advanced, the distal end (1232) of the push rod (1230) comes into contact with the marker (210). As a result, when the push rod (1230) is advanced, the marker (210) is also advanced.

In particular, as shown in FIG. 13, as the marker (210) is advanced, it is driven along the flexible strip (1210), thereby reducing the size of the retaining cavity (1250). More specifically, the marker (210) is advanced along the flexible strip (1210) and up the flexible ramp such that the push rod (1230) captures an increased length of the flexible strip (1210). The push rod (1230) is advanced until the marker (210) is driven through the cannula aperture (1240) such that the marker (210) is deployed in the biopsy site.

Once the marker (210) is deployed, the push rod (1230) may be withdrawn until the push rod (1230) is behind the flexible strip (1210) and no longer retaining the proximal end (1234) of the flexible strip (1210). As previously discussed, while in the preliminary position and while the marker (210) is being deployed, the push rod (1230) depresses the flexible strip (1210). According to such an exemplary embodiment, the flexible strip (1210) is formed of a resilient material that is configured to spring back to a shape when not depressed by the push rod (1230). Thus, the push rod (1230) may temporarily retain the flexible strip (1210) until it is no longer in contact with the flexible strip (1210).

Thereafter, the flexible strip (1210) will automatically return to its un-depressed state when the push rod is removed, as shown in FIG. 14. According to the present exemplary embodiment, as the flexible strip (1210) returns to its un-depressed state, it obstructs the cannula aperture (1240). With the cannula aperture (1240) thus obstructed, the flexible strip (1210) minimizes the possibility that the marker (210) may fall partially or completely back into the deployment device (1200).

As seen in FIGS. 15A and 15B, the push rod (1230) may be advanced slightly after the flexible strip (1210) is released from its depressed state to thereby securely close the cannula aperture (1240). As seen in FIG. 15A, as the push rod (1230) is again advanced, the push rod (1230) secures the flexible strip (1210) to the cannula (1220). More specifically, the push rod (1230) maintains the proximal end (1234) of the flexible strip (1210) on the side of the cannula aperture (1240). Thus, as seen in FIG. 15B, the flexible strip (1210) is located between the push rod (1230) and the cannula (1220) on the side of the cannula aperture (1240), thereby securely closing the cannula aperture (1240). The deployment device (1200) may thus be withdrawn while minimizing the possibility that the marker (210) will fall partially or completely into the deployment device (1200), and thus be dragged out.

Figure 16:
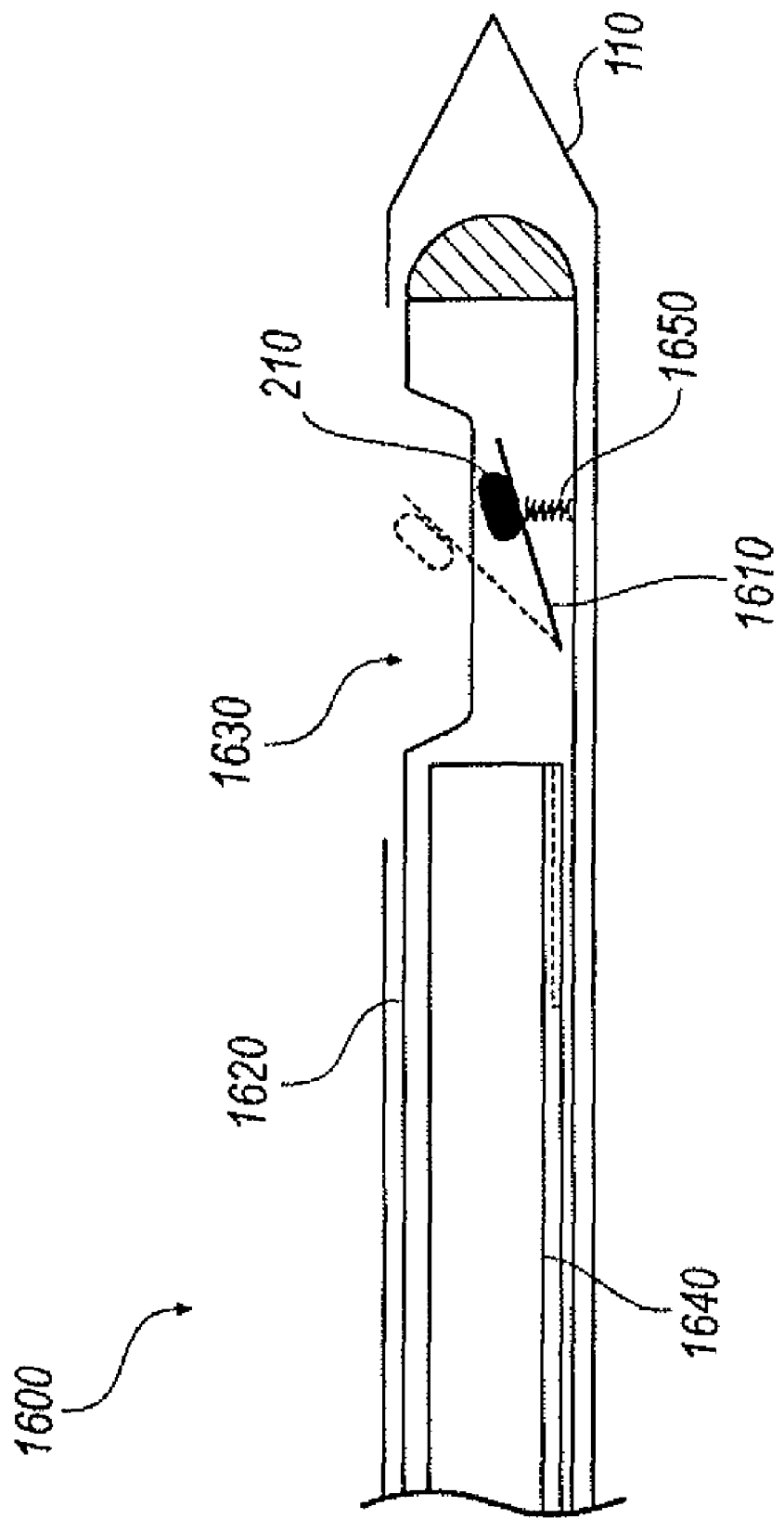
FIG. 16 illustrates a cross-sectional view of an alternative embodiment of a deployment device according to one exemplary embodiment.

FIG. 16 illustrates a deployment device (1600) according to one exemplary embodiment. As shown in FIG. 16, the deployment device (1600) includes an arm (1610) that is pivotally connected to an internal surface of a cannula (1620). One or more biasing elements (1650), such as a spring, are secured to the arm (1610) to move the arm (1610) from a pre-deployment position to a deployment position (shown in phantom). A marker (210) is positioned on a surface of the arm (1610). The cannula (1620) further has a cannula aperture defined therein (1630), where the aperture (1630) is positioned over the arm (1610). The deployment device (1600) may be introduced through the working channel (110) of a biopsy device.

The deployment device (1600) further includes a selectively retractable cover (1640). When the deployment device (1600) is in a first, pre-deployment position, the cover (1640) is positioned over the arm (1610) that is carrying the marker (210). A slot (1642) is formed on a bottom portion of cover (1640) to permit cover (1640) to pass over the arm (1610). When the sleeve extends over the arm (1610), arm (1610) is held down such that the marker (210) is retained within the deployment device (1600). However, the cover (1640) may be selectively retracted, such that the biasing element (1650) pivots the arm (1610) upwardly, protruding the marker (210) out of the aperture (1630). Once deployed, the cover (1640) may be slid back over the arm (1610) and extends past the aperture (1630) to the distal end of cannula (1620). Thus, the cover (1640) dislodges the marker (210) from the arm (1610) and obstructs the aperture (1630) thereby preventing the marker (210) from re-entering the deployment device (1600).

In another embodiment, deployment device (1600) may be used with a cannula within a cannula system (e.g., a cutting instrument). FIG. 16 further illustrates the cannula with a cannula system wherein the cover (1640) is embodied as the inner cutting instrument element. The distal end of cover (1640) may then be used to hold down the arm (1610).

The preceding description has been presented only to illustrate and describe exemplary embodiments. It is not intended to be exhaustive or to limit the disclosure to any precise form disclosed. Many modifications and variations are possible in light of the above teaching. It is intended that the scope of the disclosure be defined by the following claims.

What is claimed is:

1. A marker deployment device adapted to selectively deploy at least one marker stored therein to a location external the device, comprising:
   a cannula defining an axially extending inner lumen adapted to receive at least one marker and an aperture in communication with the inner lumen;
   a manually actuatable push rod slidably received and movable within the inner lumen of the cannula, wherein the pushrod, upon actuation, is adapted to contact and urge at least one marker distally through the inner lumen of the cannula;
   a selectively opening outlet door movable between an open position and a closed position, wherein the door (i) is configured to move to the open position upon contact with at least one of the push rod and at least one marker, (ii) obstructs at least a portion of the aperture when in the closed position and (iii) is biased toward the closed position such that the door moves to the closed position after a marker is deployed through the aperture to prevent the marker from re-entering the cannula upon deployment; and
   an inclined surface positioned within the inner lumen of the cannula adjacent to the aperture, wherein the inclined surface is adapted to guide at least one marker from the inner lumen toward and through the aperture as the marker is urged by the push rod.

2. The device of claim 1, wherein the outlet door is hinged to an outer wall of the cannula and extends at least partially over the aperture when in the closed position.

3. The device of claim 1, wherein the outlet door is defined by a portion of an outer wall of the cannula adjacent the aperture and extends at least partially over the aperture when in the closed position.

4. The device of claim 3, wherein the interface between the outlet door and the outer wall of the cannula defines a flexible hinge.

5. The device of claim 4, wherein the cannula further includes an internal wall positioned adjacent the aperture.

6. The device of claim 5, wherein the internal wall is inclined so as to form the inclined surface within the inner lumen of the cannula.

7. The device of claim 3, wherein the outlet door extends away from the internal lumen of the cannula when in the open position.

8. The device of claim 1, wherein at least a distal end of the push rod is flexible.

9. The device of claim 1, wherein the push rod is sized so as to partially extend out of said aperture when fully actuated.

10. The device of claim 1, wherein said push rod is substantially rigid but includes a flexible tip.

11. The device of claim 1, further comprising at least one marker stored within the inner lumen of the cannula.

12. The device of claim 11, wherein the cross section of the pushrod is less than the cross section of the at least one marker.

* * * * *